United States Patent [19]

Spotorno et al.

[11] Patent Number: 5,458,649
[45] Date of Patent: Oct. 17, 1995

[54] TWO-PART HIPJOINT SOCKET

[75] Inventors: Lorenzo Spotorno, Finale Ligure, Italy; Rudolf Koch, Frauenfeld; Roland Willi, Neftenbach, both of Switzerland

[73] Assignees: Sulzer Medizinaltechnik AG, Winterthur; Protek AG, Muensingen-Bern, both of Switzerland

[21] Appl. No.: 114,875

[22] Filed: Aug. 31, 1993

[30]   Foreign Application Priority Data

Sep. 2, 1992  [EP]   European Pat. Off. .............. 92810669

[51] Int. Cl.⁶ ..................................................... A61F 2/32
[52] U.S. Cl. .................................. 623/22; 623/18
[58] Field of Search ................................. 623/16, 18, 19, 623/22, 23

[56]          References Cited

U.S. PATENT DOCUMENTS 5,092,897  3/1992  Forte ........................................ 623/22

FOREIGN PATENT DOCUMENTS

| 0053794 | 6/1982 | European Pat. Off. | 623/22 |
|---|---|---|---|
| 0237751 | 9/1987 | European Pat. Off. | 623/22 |
| 0242633 | 10/1987 | European Pat. Off. | 623/22 |
| 0351545 | 1/1990 | European Pat. Off. | 623/22 |
| WO85/00284 | 1/1985 | WIPO | 623/22 |
| WO88/07845 | 10/1988 | WIPO | 623/22 |

*Primary Examiner*—David Isabella
*Attorney, Agent, or Firm*—Townsend and Townsend and Crew

[57]         ABSTRACT

A hipjoint socket has an outer cup and an inner cup disposed within and secured to the outer cup. The inner cup has a hemispherical bearing surface which is concentric with an axis and terminates at the end face, which is perpendicular to the axis. An open groove formed in the end face is concentric with the axis. A closed ring has axially relatively longer and shorter portions and a cylindrical guiding surface having a diameter about equal to a diameter of the hemispherical guiding surface. The ring includes tongues engaging the groove and thereby securing the ring to the inner cup when the ring abuts the end face. The tongues are able to slide along the groove and position the cylindrical guiding surface concentric with the axis and substantially contiguous with an end of the hemispherical bearing surface at the end face. The ring can be rotated relative to the inner cup upon the implantation of the socket to position the relatively longer ring portion on the socket where it prevents luxation of a femur head cooperating with the socket.

6 Claims, 3 Drawing Sheets

TWO-PART HIPJOINT SOCKET

BACKGROUND OF THE INVENTION

The invention is concerned with a two-part hipjoint socket for anchoring in the pelvic bone, such that by turning about the polar axis an outer cup may be clamped into the pelvic bone and/or an inner cup be clamped into the outer cup.

Hipjoint sockets of the kind named above are known, for example, from the European patent publications EP-B-0 237 751 and EF-B-0 242 633. In the case of the construction according to the first named EP patent it is a question of a screw socket in which both the outer cup is screwed into the pelvic bone and the inner cup which contains the actual socket cup for receiving the joint head is screwed into the outer cup. The socket according to the second of the above patents is a so-called spreader socket the outer cup of which is slit from the base up to its circumference so that individual flaps arise. By screwing in an inner cup the flaps which are provided on the outside with spikes are widened for anchoring the socket, the spikes penetrating into the bone.

Moreover the practice is known of providing a hipjoint socket or one of its cups at one part of the circumference of the equatorial base with an elevation in order to reduce or avoid the risk of luxations of the joint head under extreme deflections of the joint. In the EP Patent 0 150 198 in order to make "correct" setting of the elevation possible a two-cup socket is shown in which the inner cup carrying the elevation may be inserted in the outer cup in different angular positions. Similarly in the case of the socket according to the EP Patent 0 270 744 an asymmetrical insert may be inserted in different angular positions in an outer cup which maybe screwed in.

Since in the case of outer and/or inner cups which may be located by turning a definite final position of the generally screwed-in part or parts is not provided, it is not possible to locate asymmetries arranged on the outer or inner cups in an optimum angular position in the bone.

The problem of the invention is therefore in the case of sockets of the kind mentioned above initially to enable an optimum angular position of an elevation on the circumference of the base.

SUMMARY OF THE INVENTION

In accordance with the present invention this problem is solved by the inner cup exhibiting at the end face a base area in the form of a ring with an undercut annular groove in which a likewise annular elevation is held by fasteners and has a circular opening adapted to the actual socket cup, the elevation exhibiting along its circumference in at least one angular region a greater thickness towards the end face of the base area.

In the case of the new construction the elevation is a part separated from the inner cup—which in general is made with axial symmetry about the polar axis of the socket. The elevation may be inserted at an optimum angular position in the inner cup intraoperatively, after the latter has been fixed in its final position.

An additional advantage of the new construction consists in the possibility of producing the inner cup and the elevation from different materials.

A continuous setting of the optimum angular position is made possible if the fasteners may be anchored by force in any position of angular rotation, for example, by friction in the annular groove.

By waiving continuous setting, in addition to or instead of the frictional anchoring the elevation may in the angular region of greater thickness exhibit studs which secure it against twisting by a close fit in corresponding holes in the end face of the base area. In that case, setting of the angular position may be effected in steps by, for example, the holes being distributed at a constant angular pitch round the whole circumference of the annular base area, their angular pitch corresponding with an integral fraction of the angular pitch of the studs.

A further possibility of continuous setting of the optimum angular position with positive locking against turning results with an annular elevation of plastics into which a ring of metal, preferably titanium, is pressed and forms by a projecting collar a force-locking snap-in connection which snaps in in any position of rotation. For the generation of additional positive locking against turning, the metal ring exhibits at least one sharp point which penetrates into the inner cup with the snapping-in of the snap-in connection.

DESCRIPTION OF THE PREFERRED EMBODIMENTS

Figure 1:
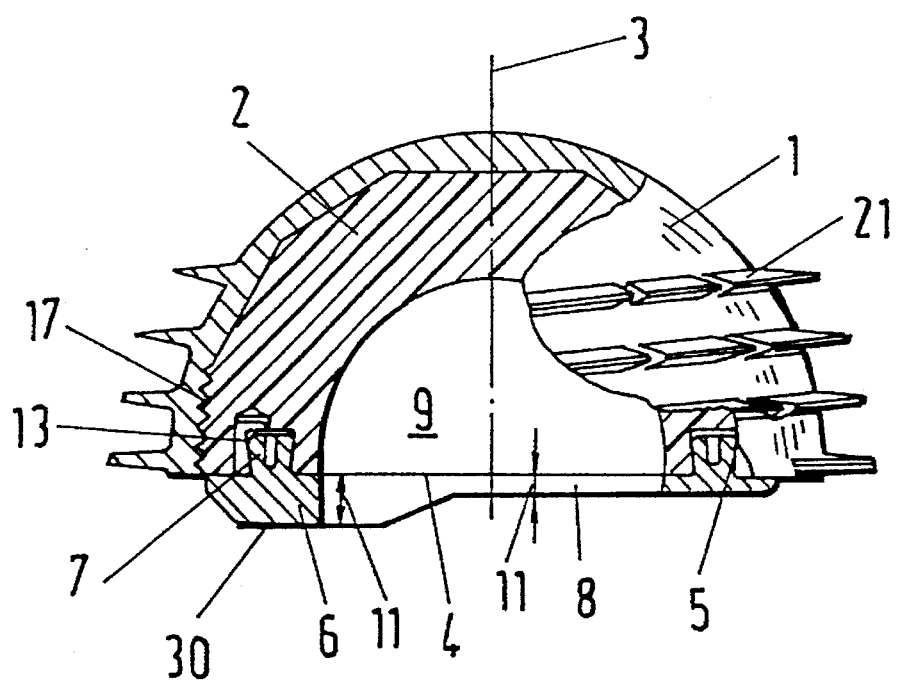
FIG. 1—shows partially in section a first embodiment of the new hipjoint socket.

The outer cup 1 of the screw socket shown in FIG. 1 is preferably manufactured from metal and has axial symmetry with respect to the polar axis 3 and carries on its outer surface a self-tapping thread 21 by which during implantation it is screwed into the pelvic bone (not shown). In its polygonally bounded cavity an inner cup 2 of plastics is inserted and fixed by means of a thread 17.

Figure 3:
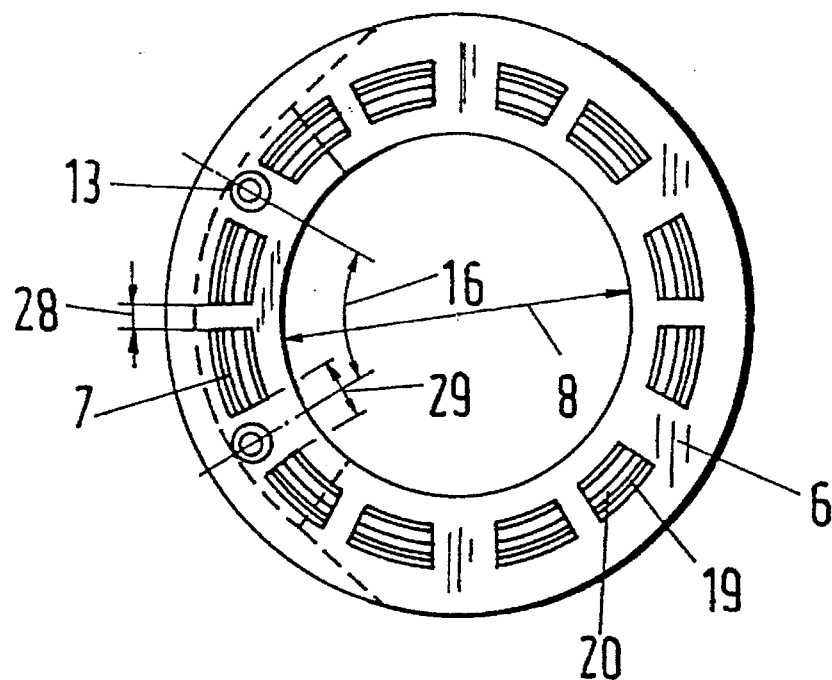
FIG. 3—is a view of the side of the annular elevation next to the inner cup—as seen in the direction of the axis of rotation of the ring.

The inner cup 2 in that area 4 of the end face of its base which surrounds in the form of a ring a socket cup 9 which serves to receive the joint head, has an undercut annular groove 5. An elevation or projection 6 is inserted in the latter and held by fasteners 7 likewise provided with undercuts; in the present example the fasteners 7 are made as portions in the form of sectors of a ring (FIG. 3) which have different distances 28 and 29 apart. One individual portion of the fasteners 7 consists of two tongues 19 running in parallel with one another and separated from one another by a slit 20 (FIG. 3). On the outside of its base the inner cup 2 has four notches 18 offset at right angles from one another, in which an instrument (not shown) is inserted for screwing the inner cup 2 into the outer cup 1.

Figure 2:
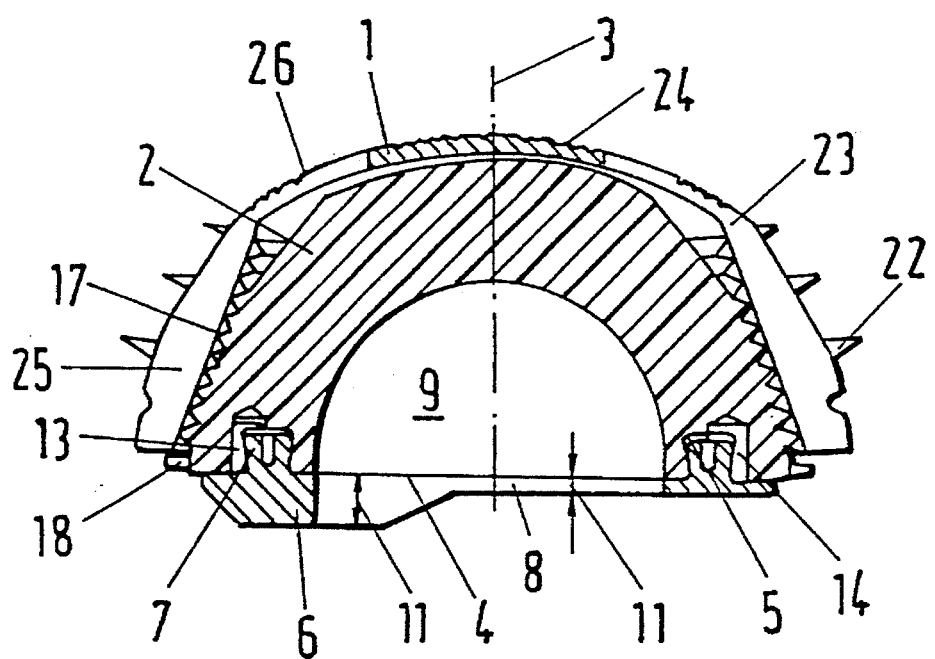
FIG. 2—shows a meridianal section in a second example.

In the case of the construction according to FIG. 2 it is a question of a so-called spreader socket; the outer cup 1 of this socket exhibits about the polar axis 3 a compact middle part 24 from which—separated by cuts running along meridian lines—individual segments 23 of the cup-like flaps extend to the base area 4. The segments 23 consist of a relatively thin-walled elastic zone 26 adjoining the middle part 24 and a thick-walled threaded part 25 which carries spikes 22 on its outer surface. Into the inside of the threaded part 25, similarly to the socket according to FIG. 1, is cut the thread 17 into which during implantation the inner cup 2, is again screwed by its like thread. Upon screwing in the inner cup 2 the cup segments 23 are widened, pressed against the pelvic bone and thus fixed, the spikes 22 penetrating into the bone.

In the region of the base the inner cup 2 according to FIG. 2 is built the same as that described above according to FIG. 1.

In both constructions the elevation or projection 6, the ring opening 8 of which is adapted to the opening in the base of the actual socket cup 9, has along its circumference angular regions of different thicknesses. While the angular region of smaller thickness extending over the greater part of the circumference serves merely as covering for the annular groove 5, the angular region 10 has a relatively greater thickness 11 and terminates in an elevated end face 30. As described initially, this elevated end face 30 reduces or avoids the risk of luxations of the joint head under extreme deflections.

For a continuous setting of an optimum angular position of the angular region 10 the tongues 19 already described are held by force, that is, merely by friction in the annular groove 5, in which case for the purpose of improved adhesion the flanks of its undercut—and/or those of the annular groove 5—may be roughened.

Figure 4:
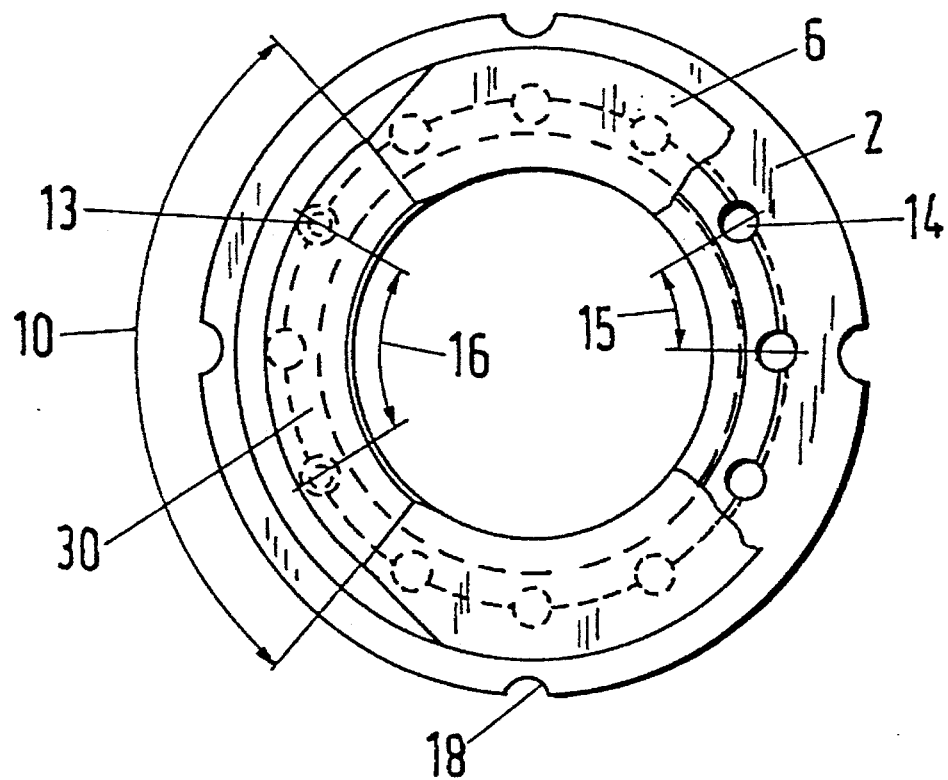
FIG. 4—is a view taken in the direction of the pole of an inner cup with an elevation inserted, the representation of which is interrupted at one part of the circumference.

If continuous adjustability is waived, in addition to or instead of the frictional connection, positive security against twisting of the elevation 6 maybe provided. In the case of the constructions shown the positive connection consists of two studs 13 arranged in the angular region 10 at the angular distance 16 apart (FIG. 4).

The studs 13 engage in holes 14 which are machined into the base area 4 of the inner cup 2. An adjustability in steps is achieved by distributing holes 14 uniformly over the whole circumference of the base area 4 having an angular pitch 15 which corresponds to an integral fraction of the angular pitch 16 of studs 13. In the example shown this angular pitch 15 is equal to half the angular pitch 16.

As may be seen from the shading in FIGS. 1 and 2 the inner cup 2 which is manufactured in general from plastics and the —here metal—elevation or projection 6 consist of different materials; through the choice of different materials, where desirable or necessary, improved properties as regards, for example, strength, frictional behavior and/or wear, are achieved.

Thus, briefly summarized, the invention presents itself as follows:

The inner cup 2 which may be screwed into an outer cup 1 of a two-part hipjoint socket is provided on its base area 4 with an undercut annular groove 5. In the annular groove 5 is held an annular elevation 6 which exhibits along its circumference at least one angular region 10 having—relative to the remaining angular regions—a greater thickness 11. The angular position of the region 10 of greater thickness 11 may at least in steps be set along the circumference.

The adjustability of the angular region 10 of greater thickness 11 in its angular position relative to the inner cup 2 enables the position of this region 10 on the circumference of the inner cup 2 to be made an optimum, independently of the final position of the inner cup 2, the final position of which because of fixing by means of the thread 17 is not exactly defined.

Figure 5:
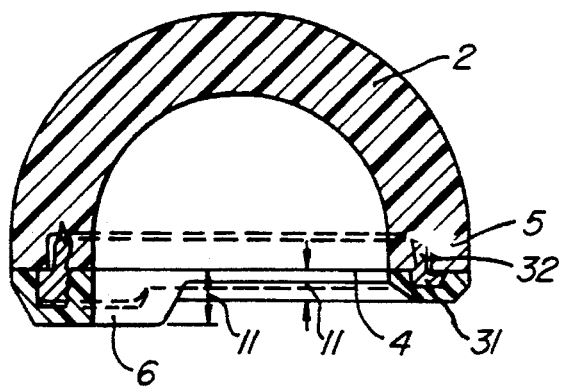
FIG. 5—is a section through an inner cup in which the annular elevation consists of a plastics body into which a metal ring with a projecting collar is pressed.
Figure 6:
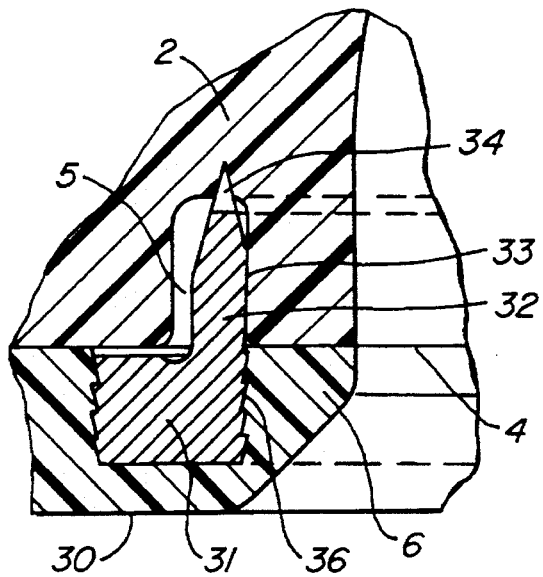
FIG. 6—is an enlarged detail from FIG. 5 and shows positive locking against turning with respect to the inner cup through a sharp point projecting from the collar.
Figure 7:
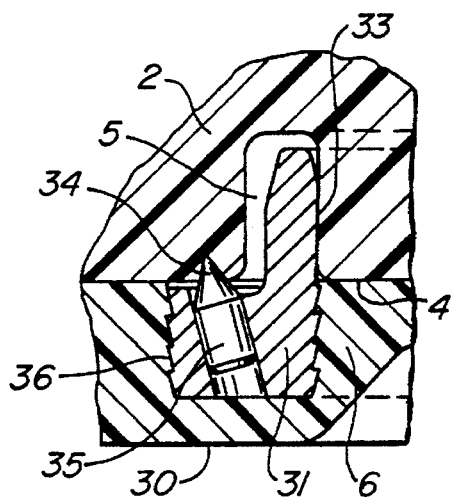
FIG. 7—is also an enlarged detail from FIG. 5 and shows positive locking against turning with respect to the inner cup through a pin with a sharp tip pressed into the metal ring.

A further embodiment is shown in FIGS. 5, 6 and 7, in which a close-fitting connection may be set continuously as regards turning between the inner cup 2 and the annular elevation or projection 6. A ring 31 of metal, preferably titanium, is pressed into the annular elevation 6 and secured by spigots and sockets 36. It imparts stability to the annular elevation 6 and at the same time forms a force-locking snap-in connection 33 by a collar 32 projecting into the annular groove 5. Upon snapping in this snap-in connection in the direction of the polar axis, at least one sharp point 34 projecting from the metal ring 31 bores itself into the edge of the inner cup 2 and thus produces a positive closure as regards turning. In FIG. 6 the sharp point 34 is made as a component of the collar 32, while in FIG. 7 the sharp point 34 is generated by a pin pressed into the metal ring.

What is claimed is:

1. A hipjoint socket comprising an outer cup for anchoring in the pelvic bone of a patient, an inner cup to be received within the outer cup and defining a hemispherical bearing surface terminating in an end face and an annular groove which is concentric with the hemispherical bearing surface formed in the end face, a thread connection between the outer cup and the inner cup for connecting the cups to each other, and a closed ring including a plurality of tongues formed and positioned to slidably engage the annular groove when the ring abuts the end face and secure the ring to the inner cup, the ring having an axially extending projection over at least one angular region of the ring and a cylindrical guiding surface which is concentric with and extends away from the hemispherical bearing surface, whereby the ring can be rotated relative to the inner cup for positioning the projection of the ring so that the projection prevents luxation of a femur head, when the femur head and the hemispherical bearing surface are in a non-load transmitting relative position, by guiding the femur head along a portion of the cylindrical guiding surface formed by the projection towards the hemispherical bearing surface of the inner cup.

2. A hipjoint socket according to claim 1 including at least two holes extending from the end face into the inner cup, and including at least two studs engaging the closed ring and extending into the holes for rotationally fixing the closed ring relative to the inner cup at a selected relative position of the projection on the inner cup.

3. A hipjoint socket according to claim 2 wherein the holes are evenly distributed about the end face, an angular spacing between adjacent holes corresponding to an integral fraction of an angular spacing between the studs.

4. A hipjoint socket according to claim 1 wherein the outer cup has an end face which is flush with the end face of the inner cup.

5. A hipjoint socket according to claim 1 wherein the outer cup has an end face which is recessed from the end face of the inner cup.

6. A hipjoint socket comprising:
    an outer cup;
    an inner cup disposed within and secured to the outer cup, the inner cup having a hemispherical bearing surface concentric with an axis and terminating at an end face of the inner cup which is perpendicular to the axis, and an open groove formed in the end face and concentric with the axis; and a closed ring having an axially relatively longer portion and an axially relatively shorter portion and defining a cylindrical guiding surface having a diameter about equal to a diameter of the hemispherical guiding surface, the ring including tongues engaging the groove and thereby securing the ring to the inner cup when the ring abuts the end face, the tongues being able to slide along the groove and positioning the cylindrical guiding surface concentric with the axis and substantially contiguous with an end of the hemispherical bearing surface at the end face;

whereby the ring can be rotated relative to the inner cup upon the implantation of the socket to position the relatively longer ring portion on the socket where it prevents luxation of a femur head cooperating with the socket.

\* \* \* \* \*